United States Patent [19]

Greene et al.

[11] Patent Number: 5,290,471

[45] Date of Patent: * Mar. 1, 1994

[54] AQUEOUS BASED PERSONAL WASHING CLEANSER

[75] Inventors: Alan P. Greene, Flemington; Barbara Y. McFarquhar, Teaneck; Rosa M. Paredes, North Bergen; Marianne E. Fenske, Westwood; Frederick S. Osmer, Parsippany, all of N.J.

[73] Assignee: Lever Brothers Company, Division of Conopco, Inc., New York, N.Y.

[ * ] Notice: The portion of the term of this patent subsequent to Sep. 4, 2007 has been disclaimed.

[21] Appl. No.: 155

[22] Filed: Jan. 4, 1993

Related U.S. Application Data

[62] Division of Ser. No. 686,902, Apr. 17, 1991, Pat. No. 5,234,619.

[30] Foreign Application Priority Data

May 1, 1990 [CA] Canada ................................ 2015868
May 4, 1990 [ZA] South Africa ....................... 90/3408

[51] Int. Cl.$^5$ .......................... C11D 9/00; C11D 9/32; C11D 1/12; C11D 1/755
[52] U.S. Cl. ..................... 252/108; 252/121; 252/550; 252/551; 252/553; 252/554; 252/557; 252/558; 252/DIG. 5; 252/DIG. 14
[58] Field of Search ............. 252/108, 121, 550, 551, 252/553, 554, 557, 558, DIG. 5, DIG. 14

[56] References Cited

U.S. PATENT DOCUMENTS

| | | | |
|---|---|---|---|
| 4,495,079 | 1/1985 | Good. | |
| 4,556,510 | 12/1985 | Holsopple. | |
| 4,617,148 | 10/1986 | Shields. | |
| 4,673,525 | 6/1987 | Small et al. | 252/172 |
| 4,954,282 | 9/1990 | Rys et al. | 252/121 |
| 5,132,037 | 7/1992 | Greene et al. | 252/108 |

FOREIGN PATENT DOCUMENTS

| | | |
|---|---|---|
| 0176330 | 4/1986 | European Pat. Off.. |
| 176330 | 4/1986 | European Pat. Off.. |
| 0217250 | 4/1987 | European Pat. Off.. |
| 249474 | 12/1987 | European Pat. Off.. |
| 2594692 | of 1987 | France. |
| 63-243200 | 10/1988 | Japan. |

OTHER PUBLICATIONS

Balsam, M. S. et al, *Cosmetics—Science & Technology*, 2nd Edition, vol. 3, Wiley & Sons, N.Y., pp. 428–429.

McCutcheon's, Functional Materials, North America Ed., 1982, p. 17.

*Primary Examiner*—Wayne Langel
*Attorney, Agent, or Firm*—James J. Farrell

[57] ABSTRACT

An aqueous based personal washing product is disclosed which when used has good cleaning ability and is particularly mild to the skin. The liquid product, containing a selected blend of surfactants and emollients, including long chain fatty acids, free isethionate salts and acyl-isethionates is particularly adapted for facial washing.

11 Claims, No Drawings

AQUEOUS BASED PERSONAL WASHING CLEANSER

This is a divisional application of Ser. No. 07/686,902 filed Apr. 17, 1991 U.S. Pat. No. 5,234,619.

BACKGROUND OF THE INVENTION

Field of the Invention

The invention is in the field of aqueous based, surfactant containing, mild cleansers, providing good foaming, moisturizing and cleaning, without excessive harshness.

The use of moisturizers in traditional washing bars is severely limited by processing constraints. Usually bars with a high content of moisturizers are sticky and cannot be easily stamped. Some of the difficulties of formulating a good personal washing product with high levels of moisturizers were eliminated by using liquid products to avoid the stamping problem.

Moisturizers have also been found to inhibit lathering. However, lathering is desirable for washing products. Further, a high concentration of moisturizers while being desirable for mildness and skin benefit has a tendency to de-stabilize liquid products.

It was thus desirable to formulate an aqueous based product containing high levels of moisturizers in combination with high levels of mild surfactants to result in a substantially stable personal washing product which is exceptionally mild to the skin; and having excellent lathering characteristics which also leaves the skin feeling smooth, silky, and moisturized.

DESCRIPTION OF THE ART

Japanese Patent JP-A-63/243,200 discloses a detergent composition containing a combination of specified acyl isethionates, higher fatty acids and N-acylglutamic acid salts. U.S. Pat. Nos. 4,556,510 and 4,617,148 both disclose liquid soaps containing polymeric thickeners along with several other surfactants including optionally sodium cocoyl isethionate. U.S. Pat. No. 4,495,079 discloses a therapeutic facial skin cleanser composed of selected surfactant mixtures and active ingredients.

There have been many different approaches to the problem of producing an aqueous based mild cleanser containing high levels of emollients/moisturizers together with combinations of mild surfactants having good viscosity, good stability, and high lathering characteristics. None of these approaches has been completely satisfactory. In many cases, stability is sacrificed to improve viscosity, or mildness is de-emphasized to improve cleaning ability or moisturizing is minimized to improve lathering.

Accordingly, it is an object of the present invention to provide an aqueous based cleansing and moisturizing product characterized by its mildness, good lathering properties acceptable viscosity and stability. This is accomplished while substantially eliminating many of the problems of the art. Other objects and advantages will appear as the description proceeds.

SUMMARY OF THE INVENTION

The attainment of the above objects is made possible by this invention which includes an aqueous based composition containing long chain acylisethionates, free isethionate salts, long chain fatty acids and moisturizing agents in specified amounts and ratios.

The inventive composition has the advantages of mildness, good moisturizing, good lathering, and excellent long term stability. Other standard ingredients such as polymeric thickeners, preservatives, co-surfactants, sequestrants, foam boosters, and the like may also be employed to advantage. The formulation may contain the following general ingredients provided an appropriate viscosity is achieved:

| Ingredients | % |
|---|---|
| long chain acylisethionate | 3–20% |
| long chain fatty acids | 2–15% |
| emollient/moisturizer | 2–15% |
| co-surfactant(s) | 2–20% |
| preservative | 0.1–1% |
| sequestrant | 0.01–0.1% |
| standard additives | 3–15% |
| water | balance |
|  | 100 |

A critical component of the formulations of this invention is a non-soap anionic surface active agent. Particularly suitable agents for this invention are the $C_8$–$C_{22}$ acyl isethionates. These esters may be prepared by the reaction between alkali metal isethionate and mixed aliphatic fatty acids having from 8 to 22 carbon atoms and an Iodine Value of less than 20. In one embodiment of the invention at least 75% of the mixed fatty acids should preferably have from 12 to 18 carbon atoms and up to 25% should have from 8 to 10 carbon atoms.

Another suitable syndet is that of alkyl glycerol ether sulfonate. Alkyl chains for this surfactant are from $C_8$ to $C_{22}$, preferably $C_{10}$ to $C_{18}$.

Free fatty acids of 8–22 carbons are desirably incorporated within the compositions of the present invention. These fatty acids are present to operate as lather enhancing agents and as skin feel, lubricity, and creaminess enhancers and, they may also be considered as emollients or moisturizers.

Thus, the composition may contain about 2–15% fatty acids and no other emollient/moisturizer. The agents may be selected from fatty acids of carbon atoms numbering 8–18 in an amount up to about 15% by weight of the composition. The most important agent is a stearic acid/palmitic acid mixture. Levels of these acids can range from 1% up to about 15%. A combination of principally palmitic and stearic acids about 40% to 75% stearic and 25% to 60% palmitic is preferred.

EMOLLIENTS/MOISTURIZERS

Moisturizers are included to provide skin conditioning benefits and to improve the mildness of the product. The selection of the levels and types of moisturizers to be incorporated into the product is done in such a manner as not to adversely affect the stability of the product or its in-use characteristics, and still deliver good moisturization and lather.

The term "moisturizer" is often used synonymously with the term emollient, and is then meant to describe a material which imparts a smooth and soft feeling to the skin surface.

One way of reducing water loss from the stratum corneum is to deposit on the surface of the skin a layer which reduces the rate of evaporation. Another method is to add hygroscopic substances, which will retain water, to the stratum corneum, to make this water available to the stratum corneum.

Both types of moisturizers as well as mixtures of these are operative in the present invention. Some examples of moisturizers are long chain fatty acids, liquid water-soluble polyols, glycerin, propylene glycol, sorbitol, polyethylene glycol, ethoxylatedpropoxylated ethers of methyl glucose and ethoxylated/propoxylated ethers of lanolin alcohol.

The moisturizers useful in the present invention are used at a level of about 5% to 35% by weight of the composition. If both fatty acids and other moisturizers are included together the preferred and more preferred levels of moisturizers are, respectively, 5% to 30% and 8% to 20%. The most preferred moisturizer is a mixture of propylene glycol or other polyol such as, for example, sorbitol and a combination of stearic and palmitic acids having a ratio of glycol to acid of 1:3 to 5:1. The moisturizer, at the above levels, provides superior moisturization. The high level of moisturizer can provide enhanced mildness.

The moisturizer to soap ratios when soap is used are preferably 9 to 1 and, more preferably, 7 to 1 or even 4 to 1.

Other moisturizers are compounds found naturally in the stratum corneum of the skin.

Moisturizers also include petrolatum, mineral oil, beeswax, silicones, lanolin and oil-soluble lanolin derivatives, saturated and unsaturated fatty alcohols and various animal and vegetable oils.

SOAPS AND OTHER INGREDIENTS

Soaps may optionally be included in the compositions of this invention as a structurant.

Soaps can be used at levels of preferably about 5% and most preferably at a level of about 2%. The soaps may be added neat or made in situ via adding a base, e.g., NaOH, to convert free fatty acids.

Free sodium isethionate in an amount of about 1% to 7% affects stability and viscosity and may also affect mildness.

Standard additives such as coloring agents, opacifying agents e.g. $TiO_2$, thickeners e.g. carbopols may be used with the invention as well as structurants which may include clays such as Bentone EW, Polymers such as polyethylene glycol, cellulosics such as carboxymethylcellulose and the like in varying amounts to insure appropriate benefits.

Sequestering agents such as EDTA, ethylene diamine tetraacetic acid trisodium salt or EHDP [disodium (1-Hydroxyethylidene) biphosphate] or mixtures of these in amounts ranging from 0.01 to as high as 1.0% preferably about 0.01 to 0.05% may be used.

Preservatives such as antimicrobials or antimold/fungus agents may be used. Examples of these are methyl paraben (p hydroxymethylbenzoate); propyl paraben (p hydroxypropylbenzoate); and Dowicil 200 [N-(3-chlorallyl) Hexaminium chloride]. These and other similar materials may be used in amounts of about 0.1% to about 0.5% and may be used separately or in combination.

Antioxidants such as, for example, butylated hydroxytoluene (BHT) may be used advantageously in amounts of about 0.01% or higher if appropriate.

A number of anionic, nonionic, cationic and amphoteric surfactants may be employed as the co-surfactant. In copending case Ser. No. 340,185 filed on Apr. 19, 1989, co-surfactant combinations in bars with acyl isethionates are disclosed. Among suitable anionic co-surfactants are the alkyl ether sulfates, alkyl ether sulfonates, sarcosinates, sulfosuccinates, taurates and combinations thereof. Among suitable amphoteric co-surfactants may be included alkylbetaines, amidropropyl betaines, amidopropyl sultaines and combinations thereof.

The relative amounts of modified isethionate esters to co-surfactants will range in the weight ratio of about 20:1 to about 0.3:1, preferably from about 5:1 to about 1:1, optimally about 1:1.

Alkyl ether sulfates of the present invention will be of the general formula $R(OCH_2CH_2)_nOSO_3\text{-}M^+$ wherein R ranges from $C_8$–$C_{20}$ alkyl, preferably $C_{12}$–$C_{15}$ alkyl, n is an integer from 1 to 20, preferably from 2 to 7, optimally about 3, and $M^+$ is a sodium, potassium, ammonium or triethanolammonium cation. Typical commercial co-surfactants of this variety are listed in the Table below:

| Trademark | Chemical Name | Physical form | Manufacturer |
| --- | --- | --- | --- |
| Alkasurf ES-60 | Sodium Laureth Sulfate | Paste | Alkaril |
| Cycloryl TD | TEA Laureth Sulfate | Paste | Cyclo |
| Standapol 125-E | Sodium Laureth-12 Sulfate | Liquid | Henkel |
| Cedepal TD407MF | Sodium Trideceth Sulfate | Paste | Miranol |

Alkyl ether sulfonates may also be employed for the present invention. Illustrative of this category is a commercial product known as Avenel S-150 commonly known as a sodium $C_{12}$–$C_{15}$ Pareth-15 sulfonate.

Another co-surfactant type suitable for use in the present invention is that of the sulfosuccinates. This category is best represented by the monoalkyl sulfosuccinates having the formula: $RO_2CCH(SO_3\text{-}Na^+)CH_2COO\text{-}M^+$; and amido-MEA sulfosuccinates of the formula: $RCONHCH_2CH_2O_2CCH(SO_3\text{-}M^+)CH_2COO\text{-}M^+$; wherein R ranges from $C_8$–$C_{20}$ alkyl, preferably $C_{12}$–$C_{15}$ alkyl and $M^+$ is a sodium, potassium, ammonium or triethanolammonium cation. Typical commercial products representative of these co-surfactants are those listed in the Table below:

| Trademark | Chemical Name | Physical form | Manufacturer |
| --- | --- | --- | --- |
| Emcol 4400-1 | Disodium Lauryl Sulfosuccinate | Solid | Witco |
| Schercopol CMSNa | Disodium Cocamido MEA Sulfosuccinate | Liquid | Scherex |
| Emcol 4100M | Disodium Myristamido MEA Sulfosuccinate | Paste | Witco |
| Schercopol OMS Na | Disodium Oleamido MEA Sulfosuccinate | Liquid | Scherex |
| Varsulf S13333 | Disodium Ricinoleamido MEA Sulfosuccinate | Solid | Scherex |

Sarcosinates may also be useful in the present invention as a co-surfactant. This category is indicated by the general formula $RCON(CH_3)CH_2CO_2\text{-}M^+$, wherein R ranges from $C_8$–$C_{20}$ alkyl, preferably $C_{12}$–$C_{15}$ alkyl and $M^+$ is a sodium, potassium, ammonium or triethanolammonium cation. Typical commercial products representative of these co-surfactants are those listed in the Table below:

| Trademark | Chemical Name | Physical form | Manufacturer |
|---|---|---|---|
| Hamposyl L-95 | Sodium Lauroyl Sarcosinate | Solid | W. R. Grace |
| Hamposyl TOC-30 | TEA Cocyl Sarcosinate | Liquid | W. R. Grace |

Taurates may also be employed in the present invention as co-surfactants. These materials are generally identified by formula $RCONR'CH_2CH_2SO_3\text{-}M^+$, wherein R ranges from $C_814$ $C_{20}$ alkyl, preferably $C_{12}\text{-}C_{15}$ alkyl, R' ranges from $C_1\text{-}C_4$ alkyl, and $M^+$ is a sodium, potassium, ammonium or triethanolammonium cation. Typical commercial products representative of these co-surfactants are those listed in the Table below:

| Trademark | Chemical Name | Physical form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2\text{-}M^+$, amidopropylbetaines of the formula $RCONH(CH_2)N^+(CH_3)_2CH_2CO_2\text{-}M^+$, and amidopropyl sultaines of the formula $RCONH(CH_2)_3N^+(CH_3)_2CH_2CH_2SO_3\text{-}M^+$, wherein R ranges from $C_8\text{-}C_{20}$ alkyl, preferably $C_{12}\text{-}C_{15}$ alkyl, and $M^+$ is a sodium, potassium ammonium or triethanolammonium cation. Typical commercial products representative of these co-surfactants are found in the Table below:

| Trademark | Chemical Name | Physical form | Manufacturer |
|---|---|---|---|
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamido-propyl Betaine | Liquid | Lonza |
| Velvetex OLB-50 | Oleyl Betaine | Paste | Henkel |

Within the broad category of co-surfactants are the alkyl sulfates, alkyl ether sulfates, alkyl ether sulfonates, sulfosuccinates, alkyl benzene sulfonates and betaines.

VISCOSITY

Viscosity of the formulation is measured with a Brookfield cone and plate H.B.D.V. II viscometer at 2 min, and 25° C. and a shear rate of $1\ s^{-1}$. The viscosity of the compositions of the invention will vary from about 100 cps to about 100,000 cps or higher if desirable. Preferably, about 5000 cps to 60,000 cps. The viscosity may also be measured by a method called Extensional Viscosity or by Rotational Viscosity. These methods are described as follows:

CONE & PLATE VISCOSITY

Cone & Plate viscosity is used to determine the viscosity of fluids in small volumes and the geometry of the instrument provides the precision necessary for the development of rheological data.

The Wells-Brookfield Cone/Plate type of viscometer is a precise torque meter which is driven at discrete rotational speeds. The torque measuring system senses the resistance to rotation caused by the fluid between the cone and a stationary flat plate. The resistance to rotation produces a torque which is proportional to the shear stress in the fluid. The amount of torque is displayed and converted to centipoise units. As mentioned above, the viscosity obtained by this method will vary from 100 cps to about 100,000 cps.

For these viscosity measurements, 2 gm of product is added to the sampling cup of the viscometer.

EXTENSIONAL VISCOSITY

Extensional viscosity is used to determine the force required to deform a material in a defined way so that differences in sample behavior can be quantified. This method is used for samples that behave as soft solids, that is, materials that have a very high viscosity at low shear rates.

The instrument used for these measurements is an Instron tensile tester fitted with a compression cell with a special probe. The probe is pushed into the sample at a constant speed while the force required to do this is measured by the compression cell.

The shape of the probe is critical to determining the rates and stress of deformation. The required shape of the probe is that of a flat thin disc attached to a much narrower shaft. The bottom surface of the disc which comes into contact with the test material is flat. The top surface of the disc is attached to the shaft and is beveled to give a tapered knife edge to the disc. This tapered design allows the test material to flow around the disc as it moves through the sample without adding any significant resistance to the measurements.

The extensional rate and stress are related to the speed of the probe and the diameter of the disc as follows:

rate = 4*probe velocity/disc diameter
stress = 3*measured force/ pi* (disc diameter squared).

Samples are prepared by filling a glass bottle with the material. Measurements are made by placing the sample under the probe, which is then pushed into the sample at a fixed rate for a distance of 20 mm. For these measurements, the probe diameter is 9 mm and the penetration speeds are 1 and 10 mm/min.

The forces generated during penetration are recorded as an analog signal on graph paper. At a constant penetration speed, the force builds to a maximum as the probe enters the material and then remains relatively constant as the probe continues to penetrate the material. This constant force is used in the stress calculations.

Under this procedure, the viscosity of the present invention is 0 cps while that of selected examples of Japanese Patent JP-A-63/243,200 mentioned above is from $2 \times 10^9$ to $1.4 \times 10^{10}$. There is some resistance of the invention composition to the penetration of the probe. However, the value is extremely small, and not within the capability of the instrument to measure.

ROTATIONAL VISCOSITY

Rotational viscosity can also be used to characterize viscous liquids, creams or soft solids.

The Carri-Med CS100 Rheometer is a commercial, conventional rotational rheometer. The measuring disc may have varying geometries (shapes) and is attached to a spindle. A constant torque is applied to the spindle and the rotational rate of the disc/plate is measured. The shear rate is thus variable and dependent upon the material under test. The measuring geometry used is a 4 cm diameter, serrated parallel plate which is used to characterize viscous materials. The gap setting is 2 mm, which maximizes the shear rate.

A sample is loaded into the gap, equilibrated for two minutes at 25° C. and then the applied torque is incremented from zero up to the instrumental maximum of 9999.9 $\mu$N m in a series of 200 steps. At each step the torque is held constant for a period of 3 s during which time the shear rate is measured. The viscosity at $1 \, s^{-1}$ is obtained directly.

Carri-Med results are given below for two samples made according to Japanese Patent # JP-A-63/243,200 and a typical formulation of this invention.

| Sample ID | | Viscosity cps |
|---|---|---|
| 90-016L | 3-28-90 | off scale |
| 90-015L | 3-28-90 | 500,000 |
| 90-026S | 4-05-90 | 80,000 |

| INVENTIVE FORMULATION Batch 90-089C Formula 90-026S | |
|---|---|
| | % wt/wt (Active Basis) |
| Sodium Cocyl Isethionate | 8.33 |
| Stearic Acid* (as Emery 420 i.e. a blend of Stearic and Palmitic acids or equivalent) | 7.92 |
| Na Soap (82/18) | 1.85 |
| Sodium Alkylbenzenesulfonate | 1.78 |
| Sodium Isethionate* | 3.92 |
| Sodium Laureth Sulfate | 3.23 |
| Disodium Cocamido MEA Sulfosuccinate | 1.62 |
| Disodium Oleamido MEA Sulfosuccinate | 1.62 |
| Propylene Glycol | 7.00 |
| Bentone EW | 0.35 |
| Methylparaben / Propylparaben / Dowicil 200 / BHT / EDTA / EHDP  Total | .45 |
| Fragrance | Q.S. |
| Water | balance to 100% |

*These amounts include that which is contained in the source of Sodium Cocyl Isethionate (Jordapon CI 70–59.5% active including 33.5% Stearic Acid and 3.4% Sodium Isethionate).

| COMPARATIVE FORMULATIONS/JAPANESE PATENT % WT/WT (Active Basis) | | | | | | |
|---|---|---|---|---|---|---|
| | 90 011L | 90 014L | 90 015L | 90 016L | 90 017L | 90 018L |
| Na Cocoylisethionate | 18 | 30 | 18 | 18 | 18 | 18 |
| Myristic acid* | 6 | — | 6 | 6 | 6 | 6 |
| Palmitic acid** | 3 | 6 | 3 | 3 | 3 | 3 |
| Na N-tallow fatty acid acyl-L-glutamate | 15 | — | — | 15 | 15 | 15 |
| Na lauroylsarcosinate | 1 | — | 1 | 1 | 1 | 1 |
| Coconut oil fatty acid diethanolamide | 2 | — | 2 | 2 | 2 | 2 |
| Propylene Glycol | 10 | — | 10 | 10 | 10 | 10 |
| Glycerol | 10 | 40 | 10 | 10 | 10 | 10 |
| Myristyl alcohol | 2 | — | 2 | 2 | 2 | 2 |
| Perfume | 0.5 | — | 0.5 | 0.5 | 0.5 | 0.5 |
| Citric acid*** | — | — | — | — | — | — |
| Linear alkyl benzene sulfonate | — | — | — | 3 | — | — |
| Disodium cocamido MEA sulfosuccinate | — | — | — | — | 1.62 | — |
| Disodium oleamido MEA sulfosuccinate | — | — | — | — | 1.62 | — |
| Sodium laureth sulfate | — | — | — | — | 3.23 | — |
| Sodium isethionate | — | — | — | — | — | 5 |
| Sodium N cocoyl L-glutamate | — | 6 | — | — | — | — |
| Water | qs | qs | qs | qs | qs | qs |

TABLE I

| BATCH | EXTENSIONAL VISCOSITY (CPS)* 1 MM/MIN–10 MM/MIN |
|---|---|
| 90-089C | 0.000–0.00 |
| 90-011L | 1.43E10** 2.04E9 |
| 90-014L | 7.01E9–3.18E9 |
| 90-015L | 5.09E9–7.0E8 |
| 90-016L | 7.65E9–8.50E8 |
| 90-017L | 1.27E10–1.15E9 |
| 90-018L | 1.34E10–1.40E9 |

LATHER

Lather evaluations are done by applying a two gram sample to the hands, followed by applying six milliliters of water. The hands are then placed palm to palm and rotated five times in a circular motion in order to dissolve the product. The product is then "worked up" by rotating the hands ten times. The resulting lather is measured by immersing the hands in a distilled water bath and lowering a funnel, whose neck has been fitted with a graduated cylinder, over the hands, so that the volume of lather can be measured.

Selected combinations of acyl isethionate and stearic/palmitic acid show improved lathering.

The following examples are designed to illustrate, but not to limit, the practice of the instant invention. Unless otherwise indicated, all percentages are by weight.

EXAMPLE 1

An aqueous based formulation according to the instant invention contains the following ingredients in the indicated amounts:

| Ingredients | % |
|---|---|
| Sodium cocoyl isethionate | 11% |
| Stearic acid or equivalent | 8% |
| Propylene glycol | 10% |
| Sodium isethionate | 5% |
| TEA lauryl sulfate | 5% |
| Sodium soap (82/18) | 2.5% |
| Sodium alkylbenzene sulfonate | 2% |
| Fragrance | 0.4% |
| Methylparaben | 0.20% |
| Propylparaben | 0.10% |
| Dowicil 200 | 0.10% |
| EDTA | 0.02% |
| EHDP | 0.02% |
| BHT | 0.008% |
| Water to | 100.00% |

PROCESS

A first batch of the formulation of the invention is conveniently prepared as follows (some of the numbers are approximate since commercial solutions vary in content):

A submix is first prepared by charging 3,200 lbs. of propylene glycol to a tank with agitation. 2,019.20 lbs. of sodium isethionate is added with slow speed agitation. 1,174.40 lbs. of a slurry containing 645.9 lbs. of sodium alkyl benzene sulfonate is then added and mixing is continued to insure uniformity. 4,000 lbs. of a 40% solution of triethanolamine lauryl sulfate is then added and mixed until uniform at a temperature of about 80° to 90° F. This submix is then set aside for future use.

13,577.76 lbs. of deionized water is heated and charged to the main mixing tank and is maintained at about 180 degrees F. The previsously prepared submix is then slowly added with slow speed agitation. 6,329.6 lbs. of a commercial preparation of sodium cocoyl isethionate is then added. This material contains 55% sodium cocoyl isethionate; 30% long chain fatty acids; 8% sodium isethionate and 7% miscellaneous; 756 lbs. of soap; 64 lbs. of methyl paraben, 32 lbs. of propyl paraben, 16.32 lbs. of EDTA and 10.56 lbs. of EHDP are added with mixing at about 5 minute intervals. 601.60 lbs. of stearic acid is then added and agitation is increased as necessary to achieve uniformity. The entire batch is then mixed at 175° to 180° F. to insure uniformity. The batch is then slowly cooled to about 115° F. 32 pounds of Dowicil is mixed into 65 lbs. of cold deionized water and this mixture is added to the batch. A previsouly prepared homogeneous fragrance mix composed of 128 lbs. of perfume and 2.56 lbs. of BHT are added and mixed into the batch. The entire batch is then mixed and cooled to reach a suitable viscosity.

Thickener slurries may, of course, optionally be used at appropriate points. These slurries may contain suitable materials such as polymers e.g. carbopol, gums and the like.

A second batch of the formulation of the invention is prepared as follows (as mentioned above, some of the numbers are approximate since commercial solutions vary in content):

A submix is first prepared by charging 2,240 lbs. of propylene glycol to a tank with agitation. 1,036 lbs. of a slurry containing 570 lbs of sodium alkyl benzene sulfonate is then added and mixing is continued to insure uniformity. 4,000 lbs. of a 25% solution of sodium laureth sulfate (2EO) is then added and the submix is mixed until uniform at a temperature of about 80° to 90° F. This submix is then set aside for future use.

A second submix is prepared. This submix is a 1.45% dispersion of hectorite clay in 7,600 pounds of cold (~80° F.) deionized water. This submix constitutes about 24% of the main batch formulation. It is made in advance with high shear mixing and set aside for future use.

In the main mixing vessel equipped with turbine agitation, 5400 lbs of deionized water is added at a temperature of 180° F. The two previously prepared submixes are then slowly added with low speed agitation. The clay dispersion is added first, the propylene glycol submix second. Next, a combined total of 3,065 lbs. of solutions of Cocamido MEA and Oleamido MEA sulfosuccinates are added to main mixing vessel. Agitation is increased and the contents of the vessel are heated back up to 165° F. Addition of 4,480 pounds of a commercial preparation of sodium cocyl isethionate follows. This material contains 57 to 62% sodium cocoyl isethionate; 31 to 36% long chain fatty acids; 0 to 4% sodium isethionate and up to 5% miscellaneous. Heating of the batch continues to 175°–180° F. 685 lbs. of soap noodles, 51 lbs. of methyl paraben, 26 lbs. of propyl paraben, 16.3 lbs. of EDTA and 10.6 lbs of EHDP are added with mixing at about 5 minute intervals. 1034 lbs. of stearic acid is then added and agitation is increased as necessary to achieve uniformity. The entire batch is then mixed at 175° F. –180° F. until uniform. The batch is then slowly cooled to about 115° F. A premix consisting of 32 lbs. of Dowicil and 64 lbs. of deionized water is added to the batch. A previously prepared homogeneous fragrance mix composed of 128 lbs. of perfume and 2.6 pounds of BHT is added and mixed into the batch. The batch is then mixed and cooled to about 100° F. 1,950 lbs. of a 57% solution of sodium isethionate is then added to the batch with continued mixing. The batch is then mixed and cooled to about 85° F. to 95° F., homogenized under pressure at about 500 to 1500 psig to a hold tank. From the hold tank, it is pumped directly to a liquid level filler.

EXAMPLE 2

Other formulations containing variations of co-surfactants are as follow

| INGREDIENT | % WT/WT FORMULA | | |
|---|---|---|---|
| | A | B | C |
| Sodium Cocoyl Isethionate | 8 | 8 | 8 |
| Stearic Acid (Emery 420 or equivalent)* | 8 | 8 | 8 |
| Sodium Isethionate* | 4 | 4 | 4 |
| Cocamidopropyl Betaine | 1 | 3 | 3 |
| Disodium Cocamido MEA Sulfosuccinate | 3 | 2 | 2 |
| Sodium Laureth Sulfate (3 EO) | 3 | — | — |
| Sodium Lauroyl Sarcosinate | — | 2 | — |
| Propylene Glycol | 7 | 7 | 7 |
| Bentone EW | 0.4 | 0.4 | 0.4 |
| Methylparaben Propylparaben Dowicil 200 BHT EDTA EHDP  Total 0.45% | 0.45 | 0.45 | 0.45 |
| Fragrance (XP 2994) | Q.S | Q.S | Q.S |
| Water | To 100 | To 100 | To 100 |

*These amounts include that which is contained in the source of sodium cocoyl isethionate (Jordapon C1-70 - 59.5% active, including 33.5% Stearic Acid and 34% sodium isethionate)

EXAMPLE 3

This Example illustrates the equivalency in mildness between a composition of the invention A and a 50% aqueous slurry of a commercial non soap detergent bar B. The percentages of B are approximate. Table I lists the two compositions.

TABLE I

| | Formulations | |
|---|---|---|
| | A % wt./wt. | B % wt./wt. |
| Sodium Cocoyl Isethionate | 10.95 | 25.0 |
| Stearic Acid* | 8.01 | 10.0 |
| Na Soap (82/18) | 2.40 | 5.5 |
| Sodium Alkylbenzenesulfonate | 2.02 | 1.0 |
| Sodium Isethionate | 5.09 | 2.4 |
| TEA Lauryl Sulfate | 5.00 | — |
| Propylene Glycol | 10.00 | — |
| Cosmedia Guar C-261 (guar gum/thickener) | 0.50 | — |
| Methylparaben | 0.20 | — |
| Propylparaben | 0.10 | — |
| Dowicil 200 | 0.10 | — |
| Viscasil 60M (silicone) | 1.00 | — |

TABLE I-continued

| | Formulations | |
|---|---|---|
| | A % wt./wt. | B % wt./wt. |
| Perfume | 0.10 | 0.5 |
| Lower Fatty acid | — | 1.5 |
| Miscellaneous solids & electrolytes | — | 1.7 |
| Water | To 100.0 | To 100.0 |

*$C_{14} = 3\%$; $C_{16} = 50\%$; $C_{18} = 47\%$

Both formulations were tested by Flex Wash. Table II lists the Flex Wash outcome which confirms the equivalently mild behavior of Formulation A to a 50% slurry of a commercial bar whose major ingredient is sodium cocoyl isethionate.

TABLE II

| | Flex Wash Test | |
|---|---|---|
| Sample Erythema | Mean Scores* Endpoint Erythema | Mean Rank |
| A | 1.385 | 13.62 |
| B | 1.385 | 13.38 |
| Statistical Analysis Rank Scores: (Wilcoxon 2 sample) | $P = 0.9580$ | |

*Mean end point scores are the mean of the evaluation scores at which the first arm received a grade "2" or greater erythema score or at the completion of nineteen washes.

THE FLEX WASH TEST

The Flex Wash procedure consists of four daily 60 second washes of the antecubital fossa (flex area of elbow). This method was designed to produce erythema quickly. Erythemal response varies only slightly with temperature and humidity fluctuations making the protocol suitable for year round testing.

Approximately 15 panelists were used as the test population. Panelist flex areas must be free of any skin condition (eczema, dryness, irritation, cuts or abrasions). Anyone taking antihistamines, anti-inflammatory drugs or topical, oral or injectable cortisone on a regular basis was excluded from the study. The panel was divided into two subgroups which were balanced for left handedness. Group I was assigned composition "A" for the left flex and "B" for the right flex. Group II reversed the order.

Following an evaluation, the panelist was instructed o moisten the left flex area. A sponge was dampened with tap water (100 ppm calcium/magnesium ions). A fixed amount of test product is applied to the sponge. The "dosed" sponge was placed in the panelist's right hand. The panelist then washed the left flex area for exactly 60 seconds (approximately 120 strokes). Thereupon, the flex was rinsed and patted dry. This washing procedure was repeated on the right arm with the appropriate composition. Washing by this procedure was repeated 4 times daily for four days and 3 times on the fifth day for a total of 19 washes. Treatment times were scheduled 1.5 hours apart. Each test site was evaluated immediately prior to washing and 4 hours after the third daily wash.

One trained assessor evaluated test sites prior to each wash and 4 hours after the third wash of the fifth day for a total of 20 evaluations. The grading scale was as follows:

0—no erythema
0.5—barely perceptible erythema
1—mild spotty erythema/no edema
1.5—mild/moderate erythema/with or without edema
2—moderate confluent erythema/with or without edema or vesiculation Each site was treated in the prescribed method until a grading of "2" or greater was attained or 19 washings had been completed. When a score of "2" or greater was attained the treatment was discontinued on that flex. The final score was then carried through for all remaining evaluations. The remaining flex was washed until either a grading of at least "2" or 19 treatments were attained, whichever was first. In this Example, the final grading is the sum total of grade scores for 20 assessments per panelist averaged over the scores from all panelists. Thus, theoretically the average score could range from 0 to 38; the lower value indicating absolutely no skin irritation with the latter being severe. In practice, scores generally range from 15 to 30.

ARM WASH

The objective is to compare the levels of irritation and/or dryness of two products on skin by assessing the changes in skin condition during exaggerated use conditions. Changes are assessed both visually and instrumentally.

The subject/panelist is in the age group of 18–55 years. The subject must have been screened for soap sensitivity and found to be sensitive to the screening solution. The target site must be free of cuts and abrasions and have a grade "0" for both erythema and dryness following a two week preconditioning period.

The subject must refrain from using creams, lotions or other types of moisturizing products over the target body area (the forearms) throughout the duration of the test.

Subjects with allergies to soap and fragrances, a history of skin disease or currently undergoing treatment for a dermatologic condition or who did not respond positively to the soap sensitivity screening test as well as subjects currently within the 2 weeks prior to the start date, taking antiinflammatory agents are excluded.

EXPERIMENTAL DESIGN

Subjects are required to precondition their skin using the conditioning product supplied under normal use conditions. This preconditioning period is two weeks in length immediately prior to the onset of the study. Use of the preconditioning product will continue throughout the study for all bathing and showering.

A group panel of 30 subjects is randomly selected based on an acceptable skin condition score for dryness and erythema established at baseline. The panel is randomly balanced for age and sex and each panelist is assigned a subject number. Laboratory wash treatments are for two morning sessions and two afternoon sessions over a four day test period. The fifth day includes two morning washes. The time interval between treatment and final assessment are standard within the panel.

Visual and tactile assessments are conducted immediately before each wash treatment to evaluate and compare changes in skin condition. A final visual assessment is conducted.

The target site is the volar surface of the forearm from the antecubital fossa (flex area) to the wrist.

Subjects are supplied with blinded product for all home bathing and are instructed to avoid washing the test site during the test week.

WASH PROCEDURE

All wash treatments are conducted by a technician. Both forearms are washed simultaneously taking care to exert equal pressure/force to each arm. Technicians alternate their treatment groups at each wash interval.

1. Using water maintained at 90° F. each forearm is wet thoroughly from the flex area to the wrist.
2. The product is placed on a wet pad and spread over the pad. The treated pad is then placed on the designated arm and is then gently glided up and down the volar surface of the forearm for two minutes.
3. The arm is rinsed under running water for 30 seconds and patted dry gently with a soft disposable towel.

VISUAL ASSESSMENT

A trained skin evaluator conducts all visual assessments. The forearms are assessed for erythema and dryness immediately prior to each wash treatment. A five point scoring scale (0-4) is used to assess skin condition for both dryness and erythema. Half point increments are used to denote slight differences between arms or for responses not warranting a full point increase.

| Dryness | Erythema |
| --- | --- |
| 0 - None | 0 - None |
| 1 - Slight flaking | 1 - Mild erythema |
| 2 - Moderate flaking/scaling | 2 - Moderate confluent erythema |
| 3 - Marked scaling, slight fissuring | 3 - Marked erythema |
| 4 - Severe scaling, fissuring | 4 - Deep erythema |

Forearms are treated until a grade "3" or greater erythema or dryness develops (end point score). Once an end point score is attained treatment of both sites is discontinued. The final visual assessment is conducted approximately three hours after the last wash.

The arm wash test described above was run comparing the following two products.

TABLE III

| Ingredients | Invention Form C | Comparative Form B |
| --- | --- | --- |
| | % wt/wt | |
| Sodium Cocoyl Isethionate | 10.95 | 25 |
| Stearic Acid | 8.01 | 10 |
| Sodium Soap | 2.40 | 5.5 |
| Sodium Alkylbenzenesulfonate | 2.02 | 1.0 |
| Sodium Isethionate | 5.09 | 2.4 |
| TEA Lauryl Sulfate | 5.00 | — |
| Propylene Glycol | 10.00 | — |
| Methylparaben | 0.20 | — |
| Propylparaben | 0.10 | — |
| Dowicil 200 | 0.10 | — |
| Fragrance | 0.10 | 0.5 |
| Lower Fatty acid | — | 1.5 |
| Miscellaneous solids & electrolytes | — | 1.5 |
| Water | To 100.00 | To 100.00 |

As in Table I, Formulation B represents a 50% slurry of a commercial bar. The percentages are thus approximate. Formulation C has no guar gum or viscasil.

The test was run to compare the mildness/irritation potential of cleanser C with a 50% slurry of a commercial bar B.

The test site was treated with one gram of slurry B or 0.5 gram of the facial cleanser C.

TABLE IV

RESULTS OF ARM WASH TEST:

| MEAN SCORES* | END POINT ERYTHEMA | END POINT DRYNESS |
| --- | --- | --- |
| Slurry B | 1.000 | 1.531 |
| Product C | 1.250 | 1.563 |

| MEAN RANK: | ERYTHEMA | DRYNESS |
| --- | --- | --- |
| Slurry B | 13.88 | 15.81 |
| Product C | 19.13 | 17.19 |
| STATISTICAL ANALYSIS OF RANK SCORES: (Wilcoxon 2 sample) | $p = 0.0981$ | $p = 0.6844$ |

*Mean end point scores are the mean of the evaluation scores at which the first arm receives a grade "2" or greater erythema score or grade "3" dryness score or at the completion of nineteen washes.

The results indicated no significant difference ($P \leq 0.05$) between Product B slurry and Product C based on the mean rank erythema and dryness scores at end point. Product C was somewhat more irritating than the slurry.

SUMMARY

The inventive composition has been evaluated in clinical studies against a slurry of a commercial bar.

In the Flex Wash against the slurry, the scores for the inventive composition were identical to the slurry scores for erythema. In the Arm Wash test, the inventive composition scores for dryness were very close to those of the slurry. There were some negative differences between the inventive composition scores and the slurry for erythema in the Arm Wash.

TABLE V

| | Slurry | Inventive Composition |
| --- | --- | --- |
| Flex Wash Erythema | 1.385 | 1.385 |
| Arm Wash Dryness | 1.531 | 1.563 |
| Arm Wash Erythema | 1.000 | 1.250 |

FACIAL WASH STUDY

The test group includes 35 subjects/panelists in the age group of 18 to 55 years. The subject must have no history of allergies or skin diseases. Panelists must refrain from using facial creams, lotions or other type of moisturizing products on their faces throughout the duration of the test period. Upon admittance to the study, each subject is provided with (2) bars of commercial soap to be used at home for a two week period prior to the start of testing.

Eligible panelists are assigned test products selected at random to equal a Right/Left or Left/Right balance in product assignment to each half-face side. Assigned Groups Include:

| Group I | Right half, Code B | Group II | Right half, Code A |
| --- | --- | --- | --- |
| | Left half, Code A | | Left half, Code B |

PROCEDURE

The schedule of wash treatments includes a single facial wash conducted both in the morning and afternoon and for four consecutive test days or a total of 7 wash treatments. Panelists are instructed not to use anything on their faces except to wash with warm water and face cloth.

Each subject has their face washed in the following manner by a technician:

a) Wet both sides of the face 10 seconds
b) An abundant lather is worked up for each test product for 10 seconds by gently rubbing a moistened pad (95–100 F) made of soft non-woven cotton cloth in each product.
c) The lathered pads are then massaged slowly but firmly over the cheek area using a counter-circular motion with a pad in each hand, washing for 60 seconds then rinsing with running water (95–100 F) for 10 seconds. This procedure is repeated a second time to equal a two-minute wash treatment. The face is then rinsed for 60 seconds with warm water and patted dry using soft disposable terry towels.

EVALUATION AND SCORING SYSTEM a) Panelist self-assessment of facial skin condition is conducted once during the study.
b) Panelists will assess their facial condition based on a global evaluation of appearance and feel of skin, comparing both left and right sides of the face.
c) Trained assessors also assess the skin condition using a grade score scale ranging from 0 to 2.5; independent parameters of evaluation will include softness and feel, degree of dryness, erythema and roughness of the face.
d) Panelists and trained assessors assess both sides of their face with the same hand at all times. The inside forearm of the opposite arm will represent a reference control site for softness.

DATA AND STATISTICS

The raw data scores are analyzed employing a paired t-test and parametric statistical design.

A half face test was conducted as described above on 35 panelists with "normal" skin types to compare the formulation of the invention and a commercial liquid soap. After one week screening period, the test period consisted of 8 wash treatments over a 4 day span with 9 evaluations done. The first evaluation was made prior to the first wash treatment and the ninth evaluation was made on the morning of the fifth day. The panelists have refrained from the use of anything but water on their faces during the study. Evaluations of various attributes were made by one expert judge and each panelist over the test period.

The results of this study are summarized in Table VI. The table indicates those evaluations for which statistically significant differences (with 95% confidence) were detected for each of the expert judge and panelist questions.

The composition A specified in Table I was compared to a commercial liquid soap with the following results.

TABLE VI

| Attribute | Results of Facial Wash | | | |
|---|---|---|---|---|
| | Judges* Composition A | Commercial Liquid | Panelists* Composition A | Commerical Liquid |
| Overall Softness | 24** | 1 | 17** | 4 |
| Erythema | 26.1** | 40.9 | | |
| Dryness | 23.4** | 43.6 | 3.6** | 5.1 |
| Roughness | 22.7** | 44.3 | 3.4** | 4.9 |
| Tightness | | | 3.0** | 4.1 |

TABLE VI-continued

| Attribute | Results of Facial Wash | | | |
|---|---|---|---|---|
| | Judges* Composition A | Commercial Liquid | Panelists* Composition A | Commerical Liquid |
| Burning | | | 2.1** | 3.3 |
| Stinging | | | 2.2** | 2.9 |
| Itching | | | 2.9** | 3.6 |

* The judges scores reflect mean ranks for all panelists. The panelists scores are individual scores based on a 0–9 scale. Mean ranks are calculated as follows: The scores for both products are arranged in a single column in ascending order. A rank of 1 is assigned to the lowest score, 2 to the second lowest score and so on until all scores have a rank. The ranks for each product are then separated into columns, summed and the average taken. This gives the mean (average) rank for each product. The better product has the lower rank.

** Significant at the 95% confidence level. In the Half Face test against the Commercial Liquid, Composition A is significantly (95% confidence level) preferred by both judges and panelists for overall softness. The judges also rated the Composition A significantly (95% confidence level) better than the Commercial Liquid for dryness, roughness, tightness, burning, itching and stinging.

This invention has been described with respect to certain preferred emobodiments and various modifications and variations in the light thereof will be suggested to persons skilled in the art and are to be included within the spirit and purview of this application and the scope of the appended claims.

What is claimed is:

1. A liquid aqueous based skin cleansing composition consisting essentially of:
   i) 3% to 20% acyl esters of isethionic acid salts, said esters being predominantly $C_8$–$C_{22}$ acyl isethionates;
   ii) 2% to 15% of at least one long chain fatty acid of 8 to 22 carbon atoms wherein the weight ratio of said acyl esters to fatty acid ranges from about 1:0.1 to about 1:10.
   iii) 2% to 20% of co-surfactant selected from the group consisting of alkyl ether sulfates, alkyl ether sulfonates, sarcosinates, sulfosuccinates, taurates, alkylbetaines, amidopropylbetaines, amidopropyl sultaines, alkylsulfonates, alkyl benzene sulfonates and mixtures thereof; and
   iv) 2% to 15% of a moisturizer component; and soap is present in an amount from 0 to 5% by weight of the composition said composition having a viscosity of about 100 to 100,000 cps.

2. A composition according to claim 1 wherein the co-surfactant is an alkyl sulfate.

3. A composition according to claim 1 wherein the moisturizer is propylene glycol.

4. A composition according to claim 1 containing about 1% to 7% of sodium isethionate.

5. A composition according to claim 1 having a viscosity of about 5,000 to 60,000 cps.

6. A composition according to claim 1 wherein said alkyl ether sulfate is selected from the group consisting of sodium laureth sulfate, TEA laureth sulfate, sodium laureth 12 sulfate, sodium trideceth sulfate and mixtures thereof;

wherein said sulfosuccinates are selected from the group consisting of disodium lauryl sulfosuccinate, disodium cocoamido MEA sulfosuccinate, disodium myristamido MEA sulfosuccinate, disodium oleamido MEA sulfosuccinate, disodium ricinoleamido MEA sulfosuccinate and mixtures thereof;

wherein said sarcosinates are selected from the group consisting of sodium lauroyl sarcosinate, TEA cocoyl sarcosinate and mixtures thereof;

wherein said taurates are selected from the group consisting of sodium methyl cocoyl taurate, sodium methyl oleoyl taurate and mixtures thereof;

wherein said alkyl betaines are selected from the group consisting of cocobetaine, oleyl betaine and mixtures thereof;

wherein said amidopropylbetaines are selected from the group consisting of cocoamidopropyl betaine, myristamidopropyl betaine and mixtures thereof; and where said amidopropyl sultaine is cocoamidopropyl hydroxysultaine.

7. A composition according to claim 1 wherein said co-surfactant is a mixture of Disodium Cocoamido MEA Sulfosuccinate and Disodium oleamido MEA Sulfosuccinate, alkyl ether sulfate and alkyl benzene sulfonate.

8. A liquid aqueous based skin cleansing composition having a formulation consisting essentially of:

| Ingredients | % |
| --- | --- |
| long chain acylisethionate | 3 to 20% |
| at least one long chain fatty acid of 8 to 22 carbon atoms | 2 to 15% |
| Moisturizer | 2 to 15% |
| Sodium isethionate | 1 to 8% |
| Co-surfactant or mixture of Co-surfactants | 2 to 20% |
| Sodium soap | 0 to 5% |
| Preservative | 0.1 to 1% |
| Sequestrant | 0.01 to 0.1% |
| Miscellaneous additives | 0.01 to 10% |
| Structurant | 0.01 to 1% |
| Water to | 100% | said composition having a viscosity of about 100 cps to about 100,000 cps.

9. A composition according to claim 8 wherein said co-surfactant is selected from the group consisting of alkyl ether sulfates, alkyl ether sulfonates, sarcosinates, sulfosuccinates, taurates, alkylbetaines, amidopropylbetaines, amidopropyl sultaines, alkyl sulfonates, alkyl benzene sulfonates, and mixtures thereof.

10. A composition according to claim 9
wherein said alkyl ether sulfate is selected from the group consisting of sodium laureth sulfate, TEA laureth sulfate, sodium laureth 12 sulfate, sodium trideceth sulfate and mixtures thereof;

wherein said sulfosuccinates are selected from the group consisting of disodium lauryl sulfosuccinate, disodium cocoamido MEA sulfosuccinate, disodium myristamido MEA sulfosuccinate, disodium oleamido MEA sulfosuccinate, disodium ricinoleamido MEA sulfosuccinate and mixtures thereof;

wherein said sarcosinates are selected from the group consisting of sodium lauroyl sarcosinate, TEA cocoyl sarcosinate and mixtures thereof;

wherein said taurates are selected from the group consisting of sodium methyl cocoyl taurate, sodium methyl oleoyl taurate and mixtures thereof;

wherein said alkyl betaines are selected from the group consisting of cocobetaine, oleyl betaine and mixtures thereof;

wherein said amidopropylbetaines are selected from the group consisting of cocoamidopropyl betaine, myristamidopropyl betaine and mixtures thereof; and wherein said amidopropyl sultaine is cocoamidopropyl hydroxysultaine.

11. A composition according to claim 8 having a viscosity of about 5,000 to 60,000 cps.

* * * * *